United States Patent [19]
Otake et al.

[11] Patent Number: 4,598,146
[45] Date of Patent: Jul. 1, 1986

[54] COMPOUND, ARUGOMYCIN
[75] Inventors: Noboru Otake, Yokohama; Hiroyuki Kawai, Urawa; Yoichi Hayakawa, Tokyo; Masaya Nakagawa, Ichikawa; Kanji Imamura; Kozo Tanabe, both of Takasaki, all of Japan
[73] Assignee: Kirin Beer Kabushiki Kaisha, Tokyo, Japan
[21] Appl. No.: 583,180
[22] Filed: Feb. 24, 1984
[30] Foreign Application Priority Data
Mar. 4, 1983 [JP] Japan .................................. 58-35663
[51] Int. Cl.[4] ........................ C07H 15/24; C12P 19/56
[52] U.S. Cl. ....................................... 536/6.4; 435/76
[58] Field of Search ........................................ 536/6.4
[56] References Cited
U.S. PATENT DOCUMENTS
4,329,450 5/1982 Wiley .................................. 536/6.4

OTHER PUBLICATIONS
European Search Report for appln. 84 10 2290.
Journal of Antibiotics, Jul. 1977, vol. 30, pp. 628–629, Wiley et al., Nogalamycin analogs having improved antititumor activity.
Journal of Antibiotics, vol. 36, Apr. 1983, pp. 451–453 Ishii et al., Decilorubicin, a new anthracycline antibiotic.
Journal of Antibiotics, vol. 36, Nov. 1983, pp. 1569–1571, Kawai et al., Arugomycin, a new Anthracycline antibiotic.

Primary Examiner—Johnnie R. Brown
Attorney, Agent, or Firm—Ladas & Parry

[57] ABSTRACT

An anthracycline compound, Arugomycin, having the physicochemical properties set forth below is produced by aerobically cultivating an Arugomycin-producing Streptomyces strain in a suitable culture medium, and recovering from the culture the anthracycline compound, Arugomycin.
(1) Color and form:
  Orange powder
(2) Melting point:
207° to 213° C. (decomposed)
(3) Specific rotatory power:
$[\alpha]_D^{25} = +112°$
(C: 0.1, chloroform:methanol=9:1)
(4) Elementary analysis (%):

|        | C    | H   | O    | N   |
|--------|------|-----|------|-----|
| Found  | 56.2 | 6.9 | 35.1 | 1.8 |
| Calcd. | 56.7 | 6.7 | 34.9 | 1.7 |

(5) Ultraviolet and visible absorption spectrum: as shown in FIG. 1.

|                    | $\lambda_{max}$ (E$_{1cm}^{1\%}$)          |
|--------------------|--------------------------------------------|
| CH$_3$OH           | 235(363), 258(167), 292(61), 476(104)      |
| 0.1N HCl + CH$_3$OH | 235(387), 258(159), 292(61), 468(110)      |
| 0.1N NaOH + CH$_3$OH | 239(302), 294(41), 543(88)                |

(6) Infrared absorption spectrum (as measured by the potassium bromide method): as shown in FIG. 2.
(7) Solubility in solvent:
  Easily soluble in a chloroform-methanol mixture, dimethyl sulfoxide, pyridine, and basic water.
  Soluble in chloroform, methanol, ethyl acetate, methyl ethyl ketone, butanol, butyl acetate, ethanol, acetone, and acidic water.
  Sparingly soluble in water.
(8) Thin layer chromatography (using "Silica Gel 60F$_{254}$" plate supplied by Merck & Co., Inc.):

| Developing solvent                              | Rf value |
|-------------------------------------------------|----------|
| Chloroform:Methanol (8:1)                       | 0.20     |
| Chloroform:Methanol:29% Aqueous ammonia (8:1:0.1) | 0.25     |
| Chloroform:Methanol:Acetic acid (8:1:0.1)       | 0.30     |
| Chloroform:Benzene:Methanol (7:2:2)             | 0.26     |

(9) NMR spectrum (400 MHz, in deuterochloroform-deuteromethanol): as shown in FIG. 3.
(10) Molecular weight (SIMS):
  m/z 1694 (M+H).

1 Claim, 3 Drawing Figures

COMPOUND, ARUGOMYCIN

BACKGROUND OF THE INVENTION

The present invention relates to a novel anthracycline compound and a process for the production thereof.

Anthracycline compunds as carcinostatic antibiotics assume an important position in medicine, and various anthracycline compounds have been proposed so far.

Generally, the physiological activities of chemicals depend greatly on their chemical structures or physicochemical properties, and there has been a continual search for anthracycline compounds of a great variety of characteristics. There has been a constant demand, therefore, also for anthracycline compounds which differ from conventional ones in terms of the aglycone moiety, saccharide moiety or substituents, or in terms of the physicochemical properties.

SUMMARY OF THE INVENTION

The present invention meets the above-mentioned demand.

More particularly, this invention provides an anthracycline compound, Arugomycin, having the physicochemical properties set forth below.

This invention also provides a process for producing the anthracycline compound, Arugomycin, which process comprises aerobically cultivating an Arugomycin-producing Streptomyces strain in a suitable culture medium, and recovering from the culture the anthracycline compound, Arugomycin, having the following physicochemical properties.

(1) Color and form:
  Orange powder
(2) Melting point:
  207° to 213° C. (decomposed)
(3) Specific rotatory powder:
  $[\alpha]_D^{25} = +112°$
  (C: 0.1, chloroform:methanol=9:1)
(4) Elementary analysis (%):

|       | C    | H   | O    | N   |
|-------|------|-----|------|-----|
| Found | 56.2 | 6.9 | 35.1 | 1.8 |
| Calcd.| 56.7 | 6.7 | 34.9 | 1.7 |

(5) Ultraviolet and visible absorption spectrum: as shown in FIG. 1.

|                    | $\lambda_{max} (E_{1cm}^{1\%})$       |
|--------------------|----------------------------------------|
| CH$_3$OH           | 235(363), 258(167), 292(61),           |

|                      | $\lambda_{max} (E_{1cm}^{1\%})$        |
|----------------------|----------------------------------------|
|                      | 476(104)                               |
| 0.1N HCl + CH$_3$OH  | 235(387), 258(159), 292(61), 468(110)  |
| 0.1N NaOH + CH$_3$OH | 239(302), 294(41), 543(88)             |

(6) Infrared absorption spectrum (as measured by the potassium bromide method): as shown in FIG. 2.

(7) Solubility in solvent:
  Easily soluble in a chloroform-methanol mixture, dimethyl sulfoxide, pyridine, and basic water.
  Soluble in chloroform, methanol, ethyl acetate, methyl ethyl ketone, butanol, butyl acetate, ethanol, acetone, and acidic water.
  Sparingly soluble in water.

(8) Thin layer chromatography (using "Silica Gel 60F$_{254}$" plate supplied by Merck & Co., Inc.):

| Developing solvent                          | Rf value |
|---------------------------------------------|----------|
| Chloroform:Methanol (8:1)                   | 0.20     |
| Chloroform:Methanol:29% Aqueous ammonia (8:1:0.1) | 0.25     |
| Chloroform:Methanol:Acetic acid (8:1:0.1)   | 0.30     |
| Chloroform:Benzene:Methanol (7:2:2)         | 0.26     |

(9) NMR spectrum (400 MHz, in deuterochloroform-deuteromethanol): as shown in FIG. 3.

(10) Molecular weight (SIMS):
  m/z 1694(M+H).

DETAILED DESCRIPTION OF THE INVENTION

Anthracycline compound, Arugomycin

Chemical structure

The anthracycline compound, Arugomycin, according to the present invention has a chemical structure as shown by the following formula (I).

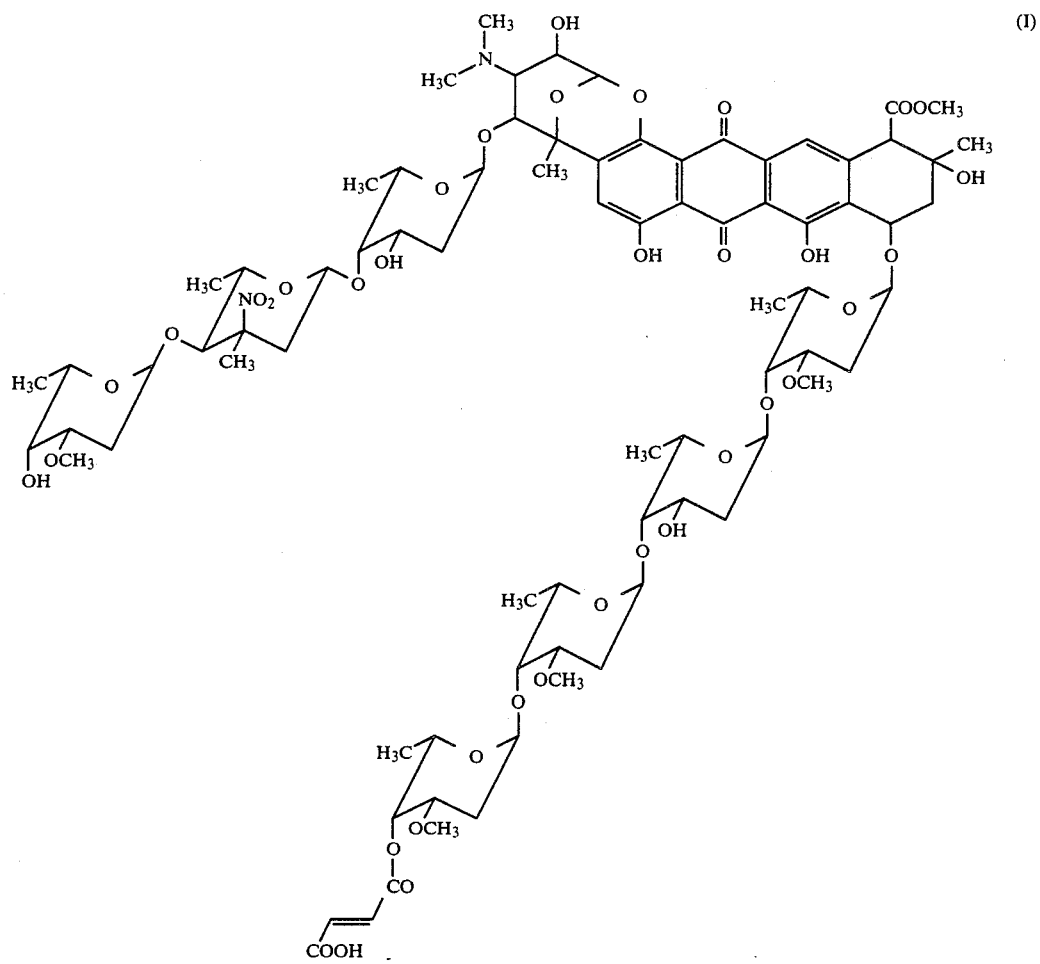

This chemical structure was determined as follows.

Arugomycin was dissolved in 40% formic acid and hydrolyzed at 85° C. for 40 minutes, whereby an aglycone moiety and a sugar moiety were obtained. Upon analysis of thin layer chromatography, ultraviolet absorption spectrum, mass spectrum and NMR spectrum, the aglycone moiety was found to have the following chemical structure wherein $R_1$ and $R_2$ are each hydrogen.

The sugar moiety was found by the decoupling of the $^1$H-NMR spectrum to comprise diginose, decilonitrose and 2-deoxyfucose.

Signals of the 4-, 6-, 7-, 2'- and 4'-positions of the aglycone moiety shown in the $^{13}$C-NMR spectrum of Arugomycin were identified, for example, by selective decoupling. The chemical shift values of the signals thus identified were compared with the corresponding data on the aglycone moiety, whereupon Arugomycin was found to have sugar chains $R_1$ and $R_2$ respectively at the 4'- and 7-positions of its aglycone moiety.

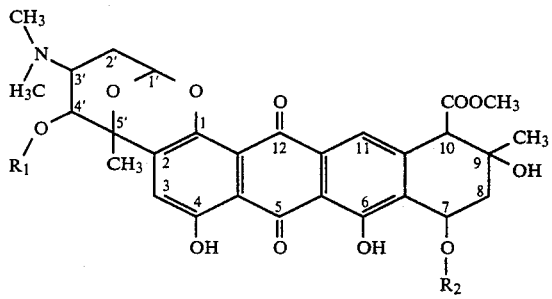

By subjecting Arugomycin to catalytic reduction with 5% Pd-BaSO$_4$ in a hydrogen stream, the bond at its 7-position is cleaved to form a red compound (a) and a colorless compound (b). These compounds (a) and (b) were found to have the structures shown below upon analysis of $^{13}$C-NMR spectra, $^1$H-NMR spectra and mass spectra.

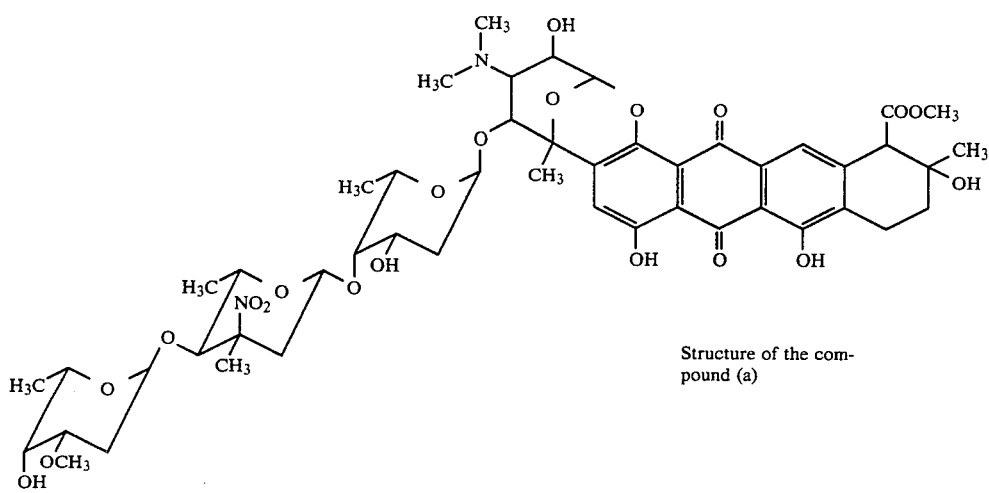

Structure of the compound (a)

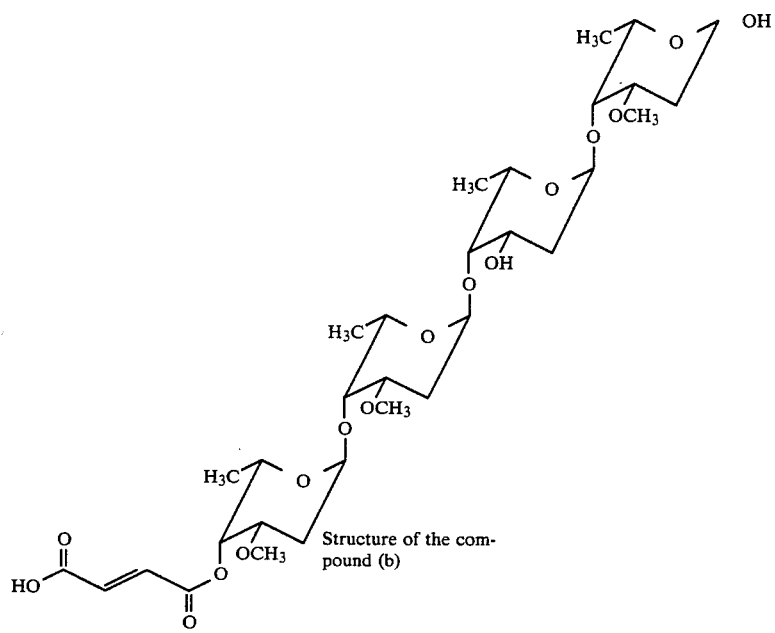

Structure of the compound (b)

Since the bonding at the 7-position of each of the compounds (a) and (b) has been found to be of α type by $^1$H-NMR spectrum, the structure of Arugomycin was determined as represented by the formula (I).

Physicochemical properties

The physicochemical properties of the anthracycline compound, Arugomycin, are as follows.

(1) color and form:
  Orange powder
(2) Melting point:
  207° to 213° C. (decomposed)
(3) Specific rotatary power:
  $[\alpha]_D^{25} = +112°$
  (C: 0.1, chloroform:methanol=9:1)
(4) Elementary analysis (%):

|        | C    | H   | O    | N   |
|--------|------|-----|------|-----|
| Found  | 56.2 | 6.9 | 35.1 | 1.8 |
| Calcd. | 56.7 | 6.7 | 34.9 | 1.7 |

Figure 1:
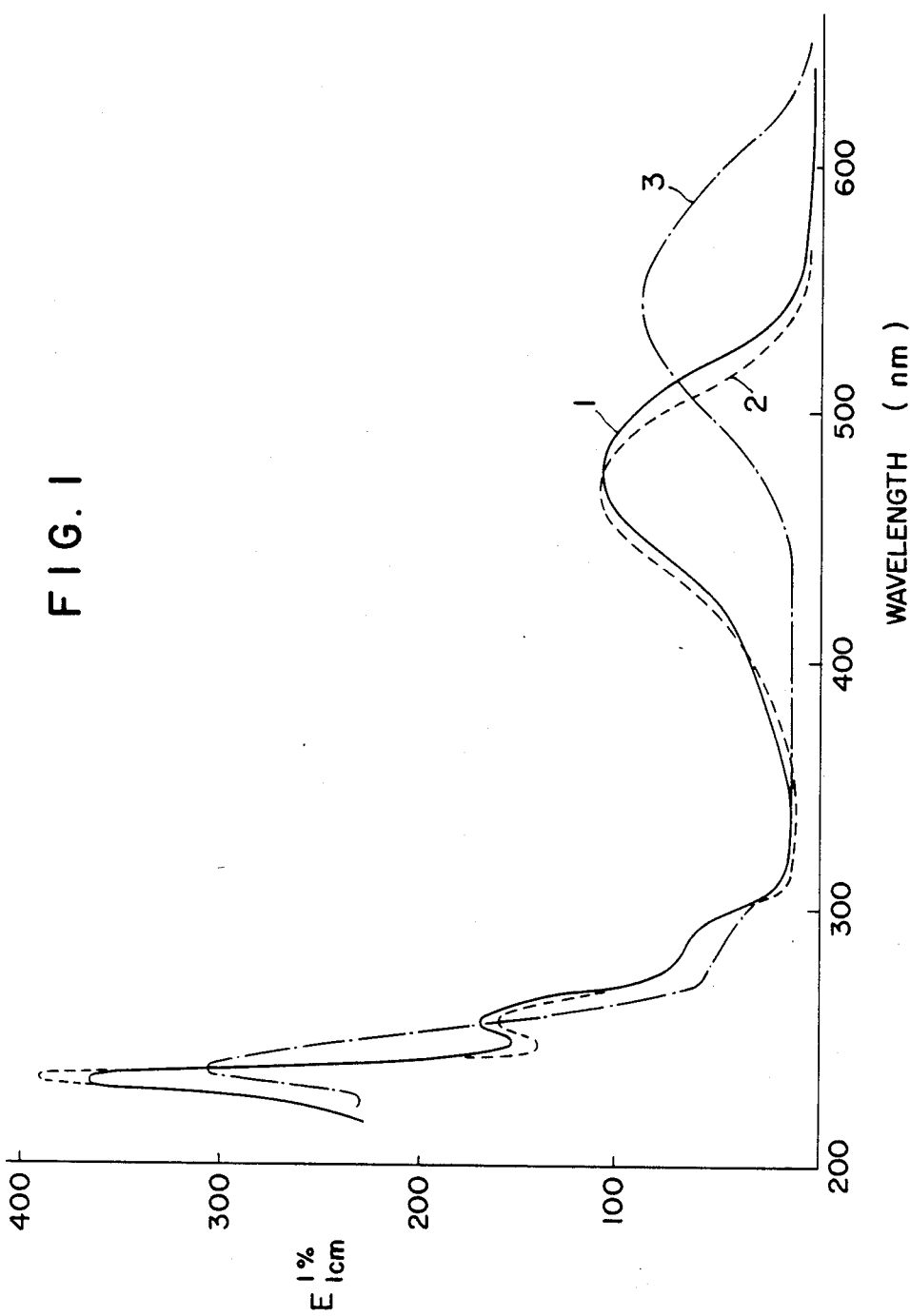
FIG. 1 shows the ultraviolet/visible absorption spectra of Arugomycin, the curve 1 showing the spectrum in methanol, the curve 2 the spectrum in methanol plus 0.1N HCl, and the curve 3 the spectrum in methanol plus 0.1N NaOH.

(5) Ultraviolet and visible absorption spectrum: as shown in FIG. 1.

|                    | $\lambda_{max}$ ($E_{1cm}^{1\%}$)          |
|--------------------|--------------------------------------------|
| CH$_3$OH           | 235(363), 258(167), 292(61), 476(104)      |
| 0.1N HCl + CH$_3$OH | 235(387), 258(159), 292(61), 468(110)     |
| 0.1N NaOH + CH$_3$OH | 239(302), 294(41), 543(88)              |

Figure 2:
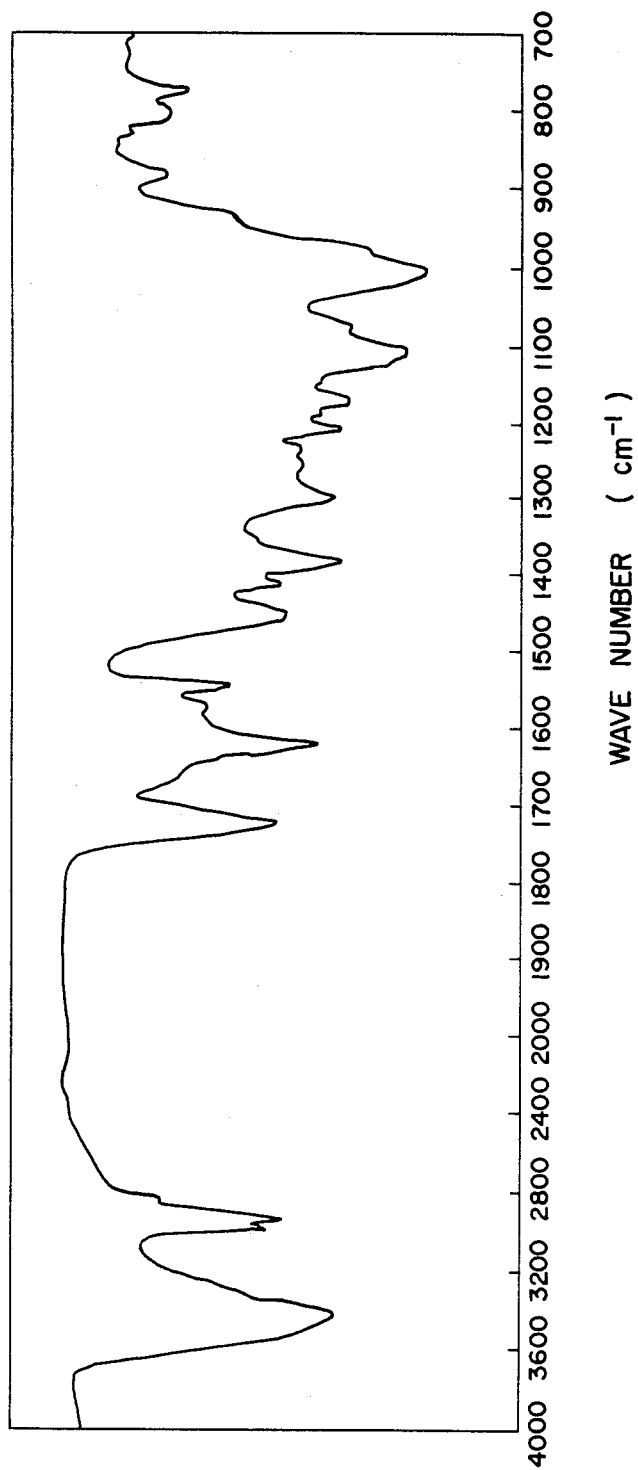
FIG. 2 shows the infrared absorption spectrum of Arugomycin.

(6) Infrared absorption spectrum (as measured by the potassium bromide method): as shown in FIG. 2.
(7) Solubility in solvent:
  Easily soluble in a chloroform-methanol mixture, dimethyl sulfoxide, pyridine, and basic water.
  Soluble in chloroform, methanol, ethyl acetate, methyl ethyl ketone, butanol, butyl acetate, ethanol, acetone, and acidic water.
  Sparingly soluble in water.
(8) Thin layer chromatography (using "Silica Gel 60F$_{254}$" plate supplied by Merck & Co., Inc.):

| Developing solvent | Rf value |
|---|---|
| Chloroform:Methanol (8:1) | 0.20 |
| Chloroform:Methanol:29% Aqueous ammonia (8:1:0.1) | 0.25 |
| Chloroform:Methanol:Acetic acid (8:1:0.1) | 0.30 |
| Chloroform:Benzene:Methanol (7:2:2) | 0.26 |

Figure 3:
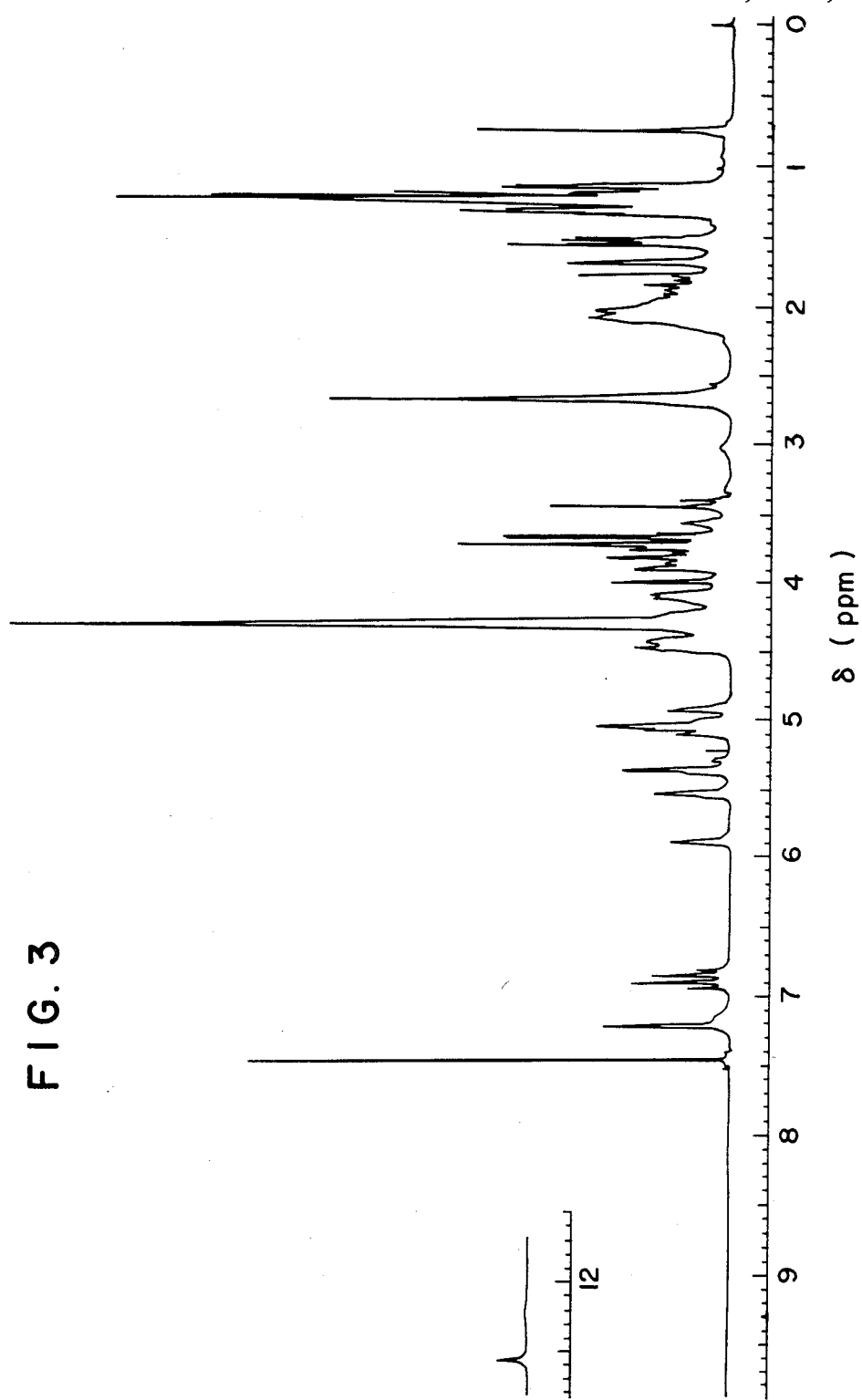
FIG. 3 shows the $^1$H-MNR spectrum of Arugomycin.

(9) NMR spectrum (400 MHz, in deuterochloroform-deuteromethanol): as shown in FIG. 3.

(10) Molecular weight (SIMS):
m/z 1694(M+H).

PRODUCTION OF ARUGOMYCIN

Outline

The anthracycline compound, Arugomycin, has been heretofore obtained only by the cultivation of microorganisms. It may be possible, however, to produce this compound by synthetic chemical or microbiological modification of related compounds, or to produce it by total chemical synthesis.

The cultivation technique uses Streptomyces strains capable of producing Arugomycin. More specifically, we have isolated a strain called *Streptomyces violochromogenes* 1089-AV$_2$ (S92) and found that this strain produces Arugomycin. Other suitable strains which produce Arugomycin can be isolated from the natural environment by customary methods for use in the isolation of antibiotics-producing microorganisms. It may also be possible to increase Arugomycin output by subjecting Arugomycin-producing microorganisms including *S. violochromogenes* 1089-AV$_2$ (S92) to irradiation by radioactive rays or to other treatments.

S92

S92, a Streptomyces strain discovered by us to be capable of producing an anthracycline compound, Arugomycin, will be described in detail hereinbelow.

(1) Origin and Accession No.

S92 is a Streptomyces strain isolated from the soil collected from a paddy field in Motoyama-cho, Kanzaki-gun, Saga-ken, Japan. This strain was deposited on Dec. 28, 1982 with the Fermentation Research Institute, Agency of Industrial Science and Technology, Ministry of International Trade and Industry of Japan, where it was assigned the accession number FERM P-6865. This strain now bears the accession number FERM BP-450 under the Budapest Treaty on the International Recognition of the Deposit of Microorganism for the Purposes of Patent Procedure.

(2) Mycological characteristics and physiological properties (a) Morphology

Aerial hyphae extend their main axis far, ramifying into short branches irregularly, and racemously in many cases (monopodial branching) while forming spore chains at the ends of the branches. The spore chain ordinarily consists of 10 to 25 spores and is tightly closed spiral in configuration (2 to 3$\mu$ in diameter, 1 to 4 turns). The spore has a smooth surface, and is of an elliptical shape 0.7 to 0.9$\mu$ in length and 0.5 to 0.6$\mu$ in width. In a certain species of culture medium (nutrient agar), substrate mycelia may ramify into short curved branches monopodially or racemously, forming at the ends of the branches spore chains (2 to 15 spores) which are curved irregularly. No other particular forms are observed. The whole cell hydrolysate contains LL-type diaminopimelic acid.

(b) Growth on various culture media

The growth of S92 on various culture media was observed in accordance with the "Manual of Method (1941)" adopted by ISP. The results obtained are summarized in Table 1.

(c) Physiological properties and carbon utilization

The physiological properties and carbon utilization of S92 are as set forth respectively in Table 2 and Table 3.

TABLE 1

Growth on Various Culture Media

| Medium | Mass color of the surface of colony | Surface & reverse side pigments of substrate mycelium | Diffusive pigment into medium |
|---|---|---|---|
| Sucrose-nitrate agar | No aerial mycelium develops | Pale orange (4ea. 5ea) | Pink (8ca. 8ea) |
| Glucose-asparagine agar | Powdery aerial mycelium develops slightly, gray and red color series (5fe. 7ih) | Brownish white-pale orange (4ea. 4ca) | None |
| Glycerol-asparagine agar | Powdery aerial mycelium develops, gray color series (d.g. 5fe) | Pale orange (4ea) Light yellowish orange (4ga) | Pale orange (4ea) Brownish white (4ea) |
| Inorganic salts-starch agar | Powdery aerial mycelium develops slightly, gray and red color series (5fe. 4ig. 4li) | Pale yellowish orange (3ga. 4ga) | None |
| Tyrosine agar | No aerial mycelium develops | Light brown (4lg.) 4ng) | Light brownish gray (4ec. 4ge) |
| Nutrient agar | No aerial mycelium develops | Light brownish gray (3ec) | Pale yellowish brown (3ic) |
| Yeast extract-malt extract agar | Powdery aerial mycelium develops slightly, gray color series (b.c) | Light yellowish orange (4ga) Dark orange (4lc. 5ic) | Pale brown (4gc) Light orange (5ia) |
| Oatmeal agar | Powdery aerial mycelium develops slightly, gray and red color series | Pale orange (4ea) Light yellowish orange (4ga) | Pale orange (4ea) Light yellowish orange (4ga) |

TABLE 1-continued

Growth on Various Culture Media

| Medium | Mass color of the surface of colony | Surface & reverse side pigments of substrate mycelium | Diffusive pigment into medium |
|---|---|---|---|
| | (3ih. 5fe) | | |

Note:
The color code is in conformity with the Color Harmony Manual, 4th Ed., issued by The Container Corporation of America (1950).

TABLE 2

Physiological Properties

| | |
|---|---|
| Growth temperature range | 20–42° C. |
| Optimum growth temperature | 27–37° C. |
| Liquefaction of gelatin | + |
| Hydrolysis of starch | + |
| Coagulation of skim milk | − |
| Peptonization of skim milk | + |
| Production of melanoid pigment | |
| Tyrosine agar medium | + |
| Peptone-yeast extract-iron agar medium | + |
| Trypton-yeast extract broth | + |

Note:
+ = positive
− = negative

TABLE 3

Carbon Utilization

| | |
|---|---|
| L-arabinose | + |
| D-xylose | + |
| D-glucose | + |
| D-fructose | + |
| Sucrose | + |
| Inositol | + |
| L-rhamnose | − |
| Raffinose | ± |
| D-mannitol | + |

Pridham and Gottlieb basal medium was used.
Note:
+ = positive utilization
± = little utilization
− = no utilization (d) Discussion 1089-AV₂ has been classified under the genus Streptomyces from the findings that the cell wall contains LL-type diaminopimelic acid and that spore chains each consisting of 10 or more spores are formed. This strain has been found to have the following five characteristic features. (a) The spore chain is in the form of a tightly closed coil. (b) The spore has a smooth surface. (c) The aerial mass is of gray and red color series. (d) The reverse side of the colony has a color varying from pale orange to light yellow and further to dark orange. (e) The melanoid pigment production is positive.

In view of these five basic features as compared with the features of known strains, 1089-AV₂ is closest to *Actinomyces (Streptomyces) violochromogenes*. Since the sole difference between 1089-AV₂ and *A. violochromogenes* is the utilization of rhamnose and raffinose, and this difference cannot be considered to differentiate species of the two strains, 1089-AV₂ has been identified as a *violochromogenes* strain. Accordingly, this strain is designated as *Streptomyces violochromogenes* 1089-AV₂.

(3) Cultivation for production of Arugomycin

The anthracycline compound, Arugomycin, can be prepared by cultivating an Arugomycin-producing Streptomyces strain aerobically in a suitable medium and recovering the objective product from the culture.

The culture media may be those containing any nutrient sources which can be utilized by Arugomycin-producing organisms. For example, glucose, sucrose, maltose, starch, oils and fats are useful as carbon sources. Examples of nitrogen sources are organic materials such as soybean meal, cotton seed meal, meat extract, peptone, dry yeast, yeast extract and corn steep liquor, and inorganic materials such as ammonium salts and nitrates, e.g., ammonium sulfate, sodium nitrate and ammonium chloride. If necessary, inorganic salts such as sodium chloride, potassium chloride, phosphates, and salts of heavy metals can also be added. In order to prevent foaming during fermentation, suitable anti-foaming agents such as silicone may be added by a conventional method.

The most suitable method of cultivation is aerobic submerged cultivation which is employed widely for the production of antibiotics. A suitable cultivation temperature is 20° to 42° C., preferably 27° to 37° C. In accordance with this method, the production output of Arugomycin reaches a maximum after 3 to 6 days of either shaking cultivation or cultivation under aeration and stirring.

A cultivated broth in which Arugomycin is accumulated can thus be obtained. In the resulting cultivated broth a part of Arugomycin is present in the mycelial cake, while a greater part thereof is present in the filtrate of the cultivated broth.

Arugomycin can be recovered from the cultivated broth by any method suitable for the recovery. One of such methods is based on extraction. For example, Arugomycin in the cultivated broth filtrate can be recovered by extraction with a water-immiscible solvent for Arugomycin such as ethyl acetate, butyl acetate, chloroform, or butanol. Arugomycin in the mycelial cake, on the other hand, can be recovered by the extraction thereof from the cake, which have been obtained by filtration or centrifugation, with chloroform, ethyl acetate, butanol, methanol, ethanol, acetone, methyl ethyl ketone, a hydrochloric acid solution, or an acetic acid solution. It is also possible to subject the cultivated broth as such to the above-mentioned extraction procedure without preliminary isolation of the mycelial cake. Countercurrent distribution using a suitable solvent may be included in the extraction methods.

Another method for recovering Arugomycin from the cultivated broth is based on adsorption. An Arugomycin-containing liquid material, such as a cultivated broth filtrate or an extract obtained by the extraction procedure described hereinbefore, is subjected, for example, to column chromatography or liquid chromatography using a suitable adsorbent such as activated carbon, alumina, silica gel or Diaion HP20 (supplied by Mitsubishi Kasei Kōg/e,ovs/y/ o K.K., Japan). The desired Arugomycin adsorbed onto the adsorbent is then eluted therefrom. The resulting Arugomycin solution is concentrated to dryness in vacuo to obtain a crude product of Arugomycin.

The crude Arugomycin product can be purified by carrying out the aforementioned extraction or adsorption procedure, if necessary, in combination, over a necessary number of times. For instance, purification can be accompanied by an appropriate combination of column chromatography using an adsorbent or a gel filter such as silica gel or Diaion HP20, liquid chromatography using a suitable solvent, and countercurrent distribution. A specific example of the purification method comprises dissolving the crude Arugomycin product in a small quantity of chloroform, applying the solution to a column packed with acidic silica, and developing the column with a suitable solvent to elute the active component of Arugomycin. The eluate is concentrated in vacuo and further eluted in a column packed with Sephadex LH20 (supplied by Phrmacia Fine Chemical AB), whereby Arugomycin is isolated as a single substance which is concentrated to dryness to obtain Arugomycin.

USES OF ARUGOMYCIN

The anthracycline compound, Arugomycin, in accordance with the present invention has carcinostatic activity and antimicrobial activity, and is therefore useful as a medicine.

Physiological activities (1) Antitumor activity

Arugomycin exhibits remarkable antitumor activity against leukemia of subject animals. For example, into $CDF_1$ mice were intraperitoneally transplanted P388 leukemia $1 \times 10^6$ cells/mouse as a suspension, and 0.5 mg/kg of Arugomycin was administered to the mice 1 day and 5 days respectively after the transplantation. The effect of Arugomycin in terms of the increase of life span (%) was 110% as calculated by determining the survival days of the control group consisting of mice administered with physiological saline solution as 100.

(2) Antimicrobial activity

Arugomycin exhibits antimicrobial activity principally against gram-positive bacteria, and the minimum inhibitory concentration (MIC) of this compound obtained by the tube dilution test was as shown in Table 4 below.

TABLE 4

| Minimum Inhibitory Concentration of Arugomycin | |
|---|---|
| Microorganism | MIC ($\mu$g/ml) |
| 1. *Bacillus subtilis* PCI 219 | 12.5 |
| 2. *Staphylococcus aureus* FDA209P | 12.5 |
| 3. *Micrococcus luteus* ATCC 9341 | 12.5 |
| 4. *Pseudomonas aeruginosa* NCTC 10490 | >100 |
| 5. *Salmonella typhimurium* IFO 12529 | >100 |
| 6. *Escherichia coli* NIHJ JC-2 | >100 |
| 7. *Saccharomyces cerevisiae* ATCC 9763 | >100 |
| 8. *Candida albicans* No. Yu 1200 | >100 |
| 9. *Candida utilis* IFO 0396 | >100 |
| 10. *Aspergillus fumigatus* IFO 4400 | >100 |
| 11. *Penicillium chrysogenum* ATCC 10002 | >100 |
| 12. *Trichophyton mentagrophytes* | >100 |

(3) Acute toxicity ($LD_{50}$)

$LD_{50}$ of Arugomycin given by intraperitoneal injection to mice was 1.75 mg/kg.

EXPERIMENTAL EXAMPLES

In the following examples, "%" is "w/v%".

EXAMPLE 1

(1) Preparation of inoculum

A medium used to grow a primary inoculum was prepared by dissolving the following ingredients in 1 liter of water and adjusting the pH of the resultant solution to 7.0.

Glucose: 0.4%
Malt extract: 1.0%
Yeast extract: 0.4%
Vitamin complex: 10 ml/liter The vitamin complex used herein was prepared by dissolving the following ingreidents in 10 ml of distilled water.

Thiamine hydrochloride: 0.5 mg
Riboflavin: 0.5 mg
Niacin: 0.5 mg
Pyridoxine hydrochloride: 0.5 mg
Inositol: 0.5 mg
Calcium pantothenate: 0.5 mg
Para-aminobenzoic acid: 0.5 mg
Biotin: 0.25 mg Each of 15-ml lots of the medium thus prepared was sterilized in a large-sized test tube and inoculated with a loopful of spores collected from a slant culture of *Streptomyces violochromogenes* 1089-AV$_2$ (S92). Each lot of the inoculated medium was shaken at 27° C. for 72 hours on a rotary shaker operating at 230 r.p.m. to preapre an inoculum.

(2) Cultivation

A fermentation medium was prepared by dissolving the following ingredients in 1 liter of water and adjusting the pH of the resultant solution to 7.0.

Starch: 2.5%
Soy bean meal: 1.5%
Dry yeast: 0.2%
Caclium carbonate (precipitated): 0.4%

Each of 100-ml lots of the fermentation medium was sterilized in a 500-ml Erlenmeyer flask, and 2 ml of the inoculum prepared as described above was added to each lot of the sterilized medium. Fermentation was carried out at 27° C. for 4 days on a rotary shaker operating at 230 r.p.m.

(3) Isolation of Arugomycin

Upon completion of the fermentation, the culture fluid was filtered. 1 liter of the filtrate, after pH adjustment to 2.0, was adsorbed onto Diaion HP20, washed with water and then with 50% methanol, and eluted with 100% methanol.

The eluate was concentrated in vacuo, and extracted with chloroform. The chloroform layer thus formed was concentrated to dryness in vacuo to obtain 1 g of a red powder (crude Arugomycin powder).

EXAMPLE 2

1 g of the crude Arugomycin powder obtained in Example 1 was dissolved in a 20:1 chloroform-methanol mixture, applied onto a column (6×60 cm) packed with 500 g of acidic silica and equilibrated with a 20:1 chloroform-methanol mixture, and eluted with a 20:1 chloroform-methanol mixture.

The active fraction obtained was concentrated to dryness in vacuo, dissolved in a 1:1 chloroform-methanol mixture, applied onto a Sephadex LH20 column equilibrated with a 1:1 chloroform-methanol mixture, and eluted with a 1:1 chloroform-methanol mixture. The active fraction thus obtained was concentrated to dryness in vacuo to yield 100 mg of an orange powder to Arugomycin.

What is claimed is:

1. An anthracycline compound, Arugomycin, having the following physicochemical properties:
   (a) Color and form:
      Orange powder;
   (b) Melting point:
      207° to 213° C. (decomposed);
   (c) Specific rotatory power:
      $[\alpha]_D^{25} = +112°$
      (C: chloroform:methanol=9:1)
   (d) Elementary analysis (%):

|  | C | H | O | N |
|---|---|---|---|---|
| Found | 56.2 | 6.9 | 35.1 | 1.8 |
| Calcd. | 56.7 | 6.7 | 34.9 | 1.7; |

(e) Ultraviolet and visible absorption spectrum: as shown in FIG. 1

|  | $\lambda_{max}\ (E_{1cm}^{1\%})$ |
|---|---|
| CH$_3$OH | 235(363), 258(167), 292,(61), 476(104) |
| 0.1N HCl + CH$_3$OH | 235(387), 258(159), 292,(61), 468(110) |
| 0.1N NaOH + CH$_3$OH | 239(302), 294(41), 543(88); |

(f) Infrared absorption spectrum (as measured by the potassium bromide method): as shown in FIG. 2;
   (g) Solubility in solvent:
      Easily soluble in a chloroform-methanol mixture, dimethyl sulfoxide, pyridine, and basic water;
      Soluble in chloroform, methanol, ethyl acetate, methyl ethyl ketone, butanol, butyl acetate, ethanol, acetone, and acidic water, Sparingly soluble in water;
   (h) Thin layer chromatograph (using "Silica Gel 60F$_{254}$" plate supplied by Merck & Co., Inc.):

| Developing solvent | Rf value |
|---|---|
| Chloroform:Methanol (8:1) | 0.20 |
| Chloroform:Methanol:29% Aqueous ammonia (8:1:0.1) | 0.25 |
| Chloroform:Methanol:Acetic acid (8:1:0.1) | 0.30 |
| Chloroform:Benzene:Methanol (7:2:2) | 0.26; |

(i) NMR spectrum (400 MHz, in deuterochloroform-deuteromethanol): as shown in FIG. 3;
   (j) Molecular weight (SIMS): m/z 1694(M+H).

* * * * *